(12) United States Patent
Fujiki

(10) Patent No.: US 10,850,074 B2
(45) Date of Patent: Dec. 1, 2020

(54) GUIDE WIRE

(71) Applicant: TERUMO KABUSHIKI KAISHA, Tokyo (JP)

(72) Inventor: Jo Fujiki, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 174 days.

(21) Appl. No.: 16/054,030

(22) Filed: Aug. 3, 2018

(65) Prior Publication Data

US 2018/0369542 A1 Dec. 27, 2018

Related U.S. Application Data

(63) Continuation of application No. PCT/JP2016/083565, filed on Nov. 11, 2016.

(30) Foreign Application Priority Data

Feb. 29, 2016 (JP) ................................. 2016-038380

(51) Int. Cl.
*A61M 25/09* (2006.01)
(52) U.S. Cl.
CPC ... *A61M 25/09* (2013.01); *A61M 2025/09083* (2013.01); *A61M 2025/09091* (2013.01); *A61M 2025/09175* (2013.01)
(58) Field of Classification Search
CPC ........ A61M 25/09; A61M 2025/09083; A61M 2025/09175; A61M 2025/09091
See application file for complete search history.

(56) References Cited

U.S. PATENT DOCUMENTS

| 5,372,144 A * | 12/1994 | Mortier | A61M 25/09 |
| | | | 600/585 |
| 2005/0027309 A1* | 2/2005 | Shiber | A61M 25/09 |
| | | | 606/159 |
| 2016/0008585 A1 | 1/2016 | Tano | |

FOREIGN PATENT DOCUMENTS

| EP | 0 551 184 A1 | 7/1993 |
| EP | 2 982 406 A1 | 2/2016 |
| JP | 2002143320 A | 5/2002 |
| WO | 2014162393 A1 | 10/2014 |

OTHER PUBLICATIONS

The extended European Search Report dated Oct. 2, 2019, by the European Patent Office in corresponding European Patent Application No. 16892679.8-1132. (7 pages).

(Continued)

*Primary Examiner* — Amber R Stiles
(74) *Attorney, Agent, or Firm* — Buchanan Ingersoll & Rooney PC

(57) ABSTRACT

A guide wire is disclosed, the guide wire including a flexible wire main body, a coil that is intermediately disposed in a longitudinal direction of the wire main body in an outer periphery of the wire main body, and a support portion that supports at least one of a distal end and a proximal end of the coil so as to be rotatable around a central axis O of the wire main body. In a natural state where an external force is not supplied to the guide wire, the support portion supports in a state where an inner peripheral portion of the coil and an outer peripheral portion of the wire main body are separated from each other.

20 Claims, 6 Drawing Sheets

(56) References Cited

OTHER PUBLICATIONS

International Search Report (PCT/ISA/210) dated Jan. 31, 2017, by the Japanese Patent Office as the International Searching Authority for International Application No. PCT/JP2016/083565.
English translation of the Written Opinion of the International Searching Authority and Search Report dated Jan. 31, 2017 in International Application No. PCT/JP2016/083565.
Office Action (Notice of Reasons for Refusal) dated Apr. 21, 2020, by the Japanese Patent Office in corresponding Japanese Patent Application No. 2018-502520 and an English Translation of the Office Action. (7 pages).

\* cited by examiner

GUIDE WIRE

CROSS-REFERENCES TO RELATED APPLICATIONS

This application is a continuation of International Application No. PCT/JP2016/083565 filed on Nov. 11, 2016, which claims priority to Japanese Patent Application No. 2016-038380 filed on Feb. 29, 2016, the entire content of both of which is incorporated herein by reference.

TECHNICAL FIELD

The present disclosure generally relates to a guide wire.

BACKGROUND DISCUSSION

A guide wire can be used when guiding a catheter for treatment of a site having difficulties in surgery, for minimally invasive treatment for a human body, or for examination such as cardioangiography. For example, when percutaneous coronary intervention (PCI) is performed, in a state where a distal end of the guide wire protrudes from a distal end of a balloon catheter under X-ray fluoroscopy, the guide wire together with the balloon catheter is inserted into the vicinity of a stenosed site of a coronary artery which serves as a target site, and the distal portion of the balloon catheter is guided to the vicinity of the vascular stenosed site.

For example, as the guide wire used for this treatment, a guide wire disclosed in JP-A-2002-143320 is known. This guide wire has a flexible wire main body (core wire), a primary coil fixed to a distal portion of the wire main body, and a secondary coil disposed on a proximal side of the primary coil and installed to cover an outer periphery of the wire main body. The secondary coil is disposed so as not be fixed to the wire main body and the primary coil. The secondary coil can be rotated independently of the wire main body and the primary coil. Accordingly, for example, if the secondary coil is caught by the vascular stenosed site, the wire main body and the distal coil can be rotationally operated.

However, according to the guide wire disclosed in JP-A-2002-143320, the wire main body and the secondary coil are separated from each other, and a gap can be formed between the wire main body and the secondary coil. Therefore, in some cases, axial misalignment occurs between the wire main body and the secondary coil. For example, in some cases, the wire main body and the secondary coil are unintentionally misaligned from each other in a radial direction. Depending on a degree of this misalignment, there is a possibility that operability may become poor.

SUMMARY

A guide wire is disclosed, which is capable of achieving excellent operability inside a steeply curved blood vessel or inside a vascular stenosed site. The guide wire disclosed here may involve the following aspects (1) to (10).

(1) A guide wire is disclosed, which includes a flexible wire main body, a tubular portion that is intermediately disposed in a longitudinal direction of the wire main body in an outer periphery of the wire main body, and that has a tubular shape, and a support portion that supports at least one of a distal portion and a proximal portion of the tubular portion from the inside to be rotatable around a central axis of the wire main body.

(2) In the guide wire in (1) described above, in a natural state where an external force is not applied to the guide wire, the support portion supports in a state where an inner peripheral portion of the tubular portion and an outer peripheral portion of the wire main body are separated from each other.

(3) In the guide wire in (1) or (2) described above, the support portion is fixed to the wire main body.

(4) In the guide wire in (3) described above, the tubular portion includes a coil formed of a wire rod wound in a spiral shape. The support portion has a cylindrical shape, and a spiral groove into which the wire rod is inserted is disposed in an outer peripheral portion of the support portion.

(5) The guide wire in (3) or (4) described above further includes a distal coil that is disposed on a distal side from the tubular portion in a distal outer peripheral portion of the wire main body, and a fixing portion that fixes a proximal portion of the distal coil to the wire main body. The support portion is formed integrally with the fixing portion.

(6) In the guide wire in (1) or (2) described above, the support portion has a cylindrical shape, and is rotatable around the central axis of the wire main body with respect to the wire main body.

(7) In the guide wire in (6) described above, the support portion and the tubular portion are fixed to each other.

(8) The guide wire in (6) or (7) described above further includes a distal coil that is disposed on a distal side from the tubular portion in a distal outer peripheral portion of the wire main body. The support portion has a cylindrical shape, and an inner diameter of the support portion is smaller than an outer diameter of the distal coil.

(9) In the guide wire in any one of (6) to (8) described above, the support portion has a tapered portion whose outer diameter gradually decreases in a direction away from the tubular portion.

(10) The guide wire in any one of (1) to (9) described above further includes a restriction portion that restricts movement of the tubular portion in the longitudinal direction of the wire main body.

According to the present disclosure, the tubular portion is rotatable with respect to the wire main body. Therefore, even if the tubular portion is caught by a stenosed site, the wire main body can be rotationally operated.

In accordance with an exemplary embodiment, the guide wire has the support portion that supports the tubular portion. Therefore, axial misalignment between the tubular portion and the wire main body can be prevented. For example, a positional relationship between the tubular portion and the wire main body can be restricted. As a result, it is possible to prevent the tubular portion and the wire main body from being unintentionally misaligned from each other in a radial direction. According to the above-described configurations, the guide wire according to the present disclosure can have excellent operability.

A guide wire is disclosed, which includes a flexible wire main body; a tubular portion that is intermediately disposed in a longitudinal direction of the wire main body in an outer periphery of the wire main body, the tubular portion having has a tubular shape; a support portion that supports at least one end portion of a distal portion and a proximal portion of the tubular portion from the inside so as to be rotatable around a central axis of the wire main body; and at least a portion of the support portion is located between the outer periphery of the wire main body and an inner periphery of the tubular portion in at least one of the distal portion and the proximal portion of the tubular portion.

A guide wire is also disclosed, which includes a flexible wire main body; a tubular portion that is intermediately disposed in a longitudinal direction of the wire main body in an outer periphery of the wire main body, and wherein the tubular portion has a tubular shape having a lumen; a support portion that supports at least one of a distal portion and a proximal portion of the tubular portion from the inside and configured to be rotatable around a central axis of the wire main body; the support portion including a protruding portion which protrudes along the central axis; and wherein the protruding portion is inserted into the lumen of the tubular portion from at least one of the distal portion and the proximal portion of the tubular portion.

DETAILED DESCRIPTION

Figure 1:
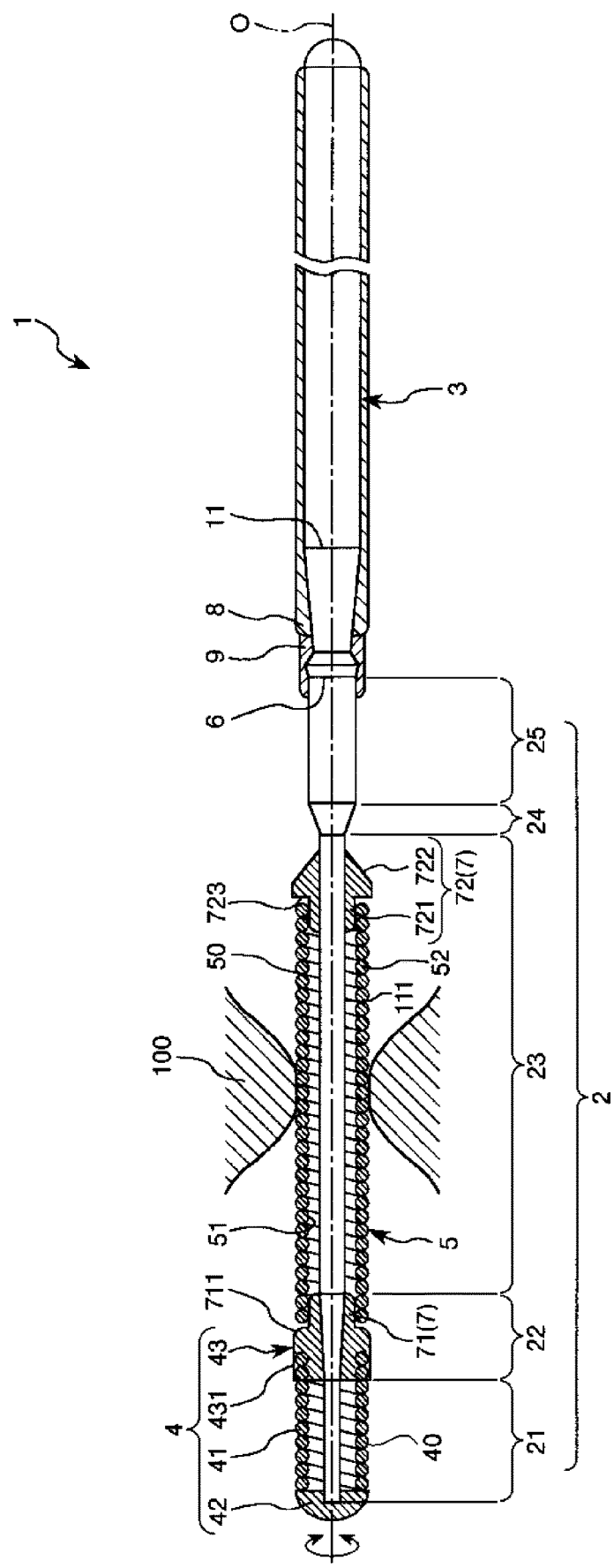
FIG. 1 is a longitudinal cross-sectional view (schematic side view) illustrating a first embodiment of a guide wire.

Set forth below with reference to the accompanying drawings is a detailed description of embodiments of a guide wire representing examples of the inventive guide wire disclosed here. In some cases, a dimension ratio in the drawings may be exaggerated and different from a ratio used in practice in order to facilitate the description.

First Embodiment

Figure 2:
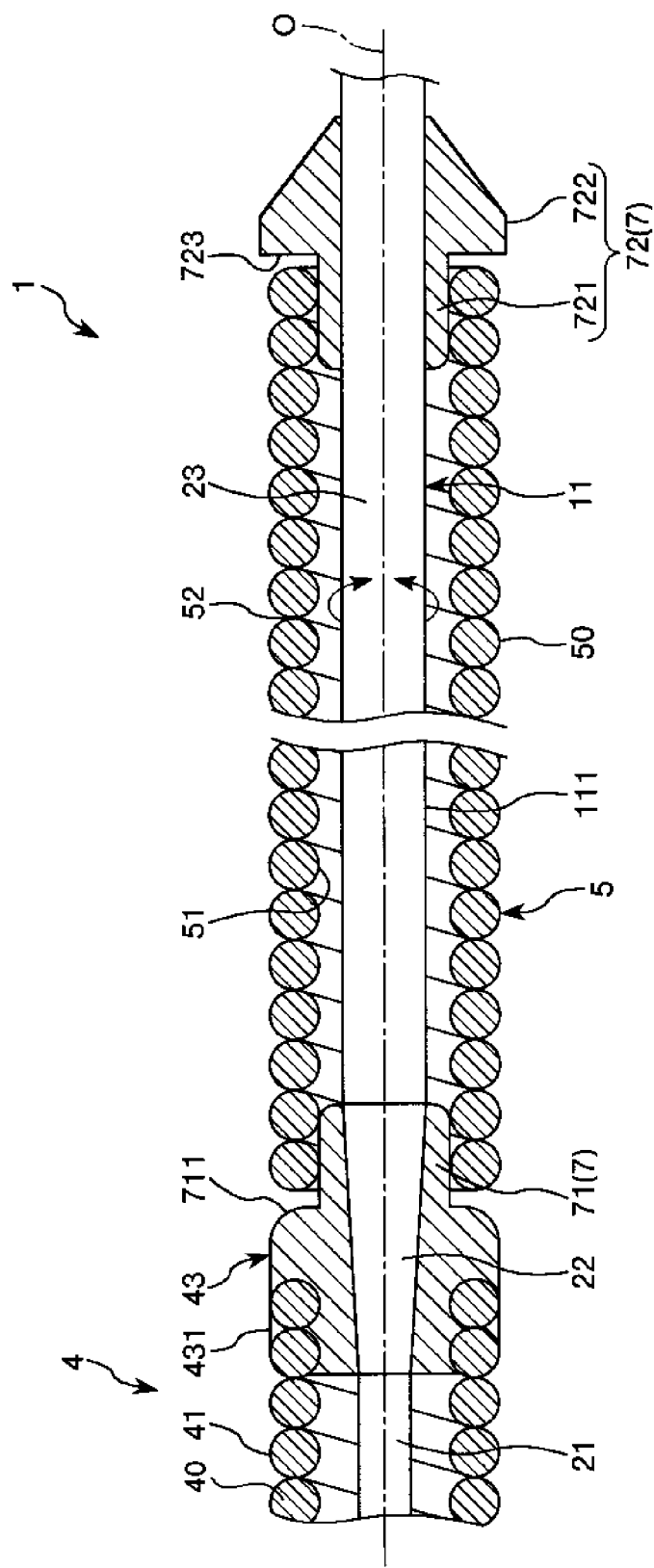
FIG. 2 is an enlarged cross-sectional view of a tubular portion and a support portion, which are illustrated in FIG. 1.

FIG. 1 is a longitudinal cross-sectional view (schematic side view) illustrating a first embodiment of a guide wire according to the present disclosure. FIG. 2 is an enlarged cross-sectional view of a tubular portion and a support portion, which are illustrated in FIG. 1. Hereinafter, for convenience of description and understanding, a right side (i.e., the side operated by an operator) in a long axis direction (or axial direction) in FIGS. 1 and 2 will be referred to as a "proximal", "proximal end", or "proximal side", and a left side (i.e., a side inserted into a living body) will be referred to as a "distal", "distal end", or "distal side". An upper side will be referred to as "upward", and a lower side will be referred to as "downward". In addition, in order to facilitate understanding, FIGS. 1 and 2 are schematically illustrated in such a manner that a length direction of the guide wire is shortened and a radial direction (thickness direction) of the guide wire is exaggerated. A ratio between the length direction and the radial direction is different from an actual ratio (the same in the drawings subsequent to FIG. 3). In addition, the guide wire according to the present disclosure achieves excellent operability in, for example, a vascular stenosed site having a decreased distance between tube walls of a blood vessel, or a site having a steeply curved blood vessel. Hereinafter, a case where the guide wire according to the present disclosure is located inside the vascular stenosed site will be described as a representative example.

A guide wire 1 illustrated in FIG. 1 can be a catheter guide wire used by being inserted into a lumen of a catheter (including an endoscope), and includes a first wire 2 located on a distal side, a flexible wire main body 11 formed by joining (connecting) a second wire 3 located on a proximal side of the first wire 2 to the first wire 2, a distal member 4 having a coil 41 fixed to a distal portion of the wire main body 11 by using fixing members 42 and 43, a coil 5 (tubular member) disposed on a proximal side of the coil 41, on an outer periphery of the wire main body 11, and a support portion 7. A total length of the guide wire 1 is not particularly limited. However, the total length of the guide wire 1 may be, for example, approximately 200 mm to 5,000 mm. In addition, an outer diameter of the guide wire 1 is not particularly limited. However, the outer diameter of the guide wire 1 can be, for example, approximately 0.2 mm to 1.2 mm.

In accordance with an exemplary embodiment, the first wire 2 may include a flexible or elastic wire rod (core material). A length of the first wire 2 is not particularly limited. However, the length of the first wire 2 can be, for example, approximately 20 mm to 1,000 mm.

According to the present embodiment, the first wire 2 has a portion whose outer diameter is constant (constant outer diameter portion), and a portion having a tapered shape whose outer diameter gradually decreases in a distal direction (gradually decreasing outer diameter portion) (tapered portion). In the illustrated configuration, sequentially (or arranged) from the proximal side to the distal side, the first wire 2 has a constant outer diameter portion 25, a tapered portion (proximal side tapered portion) 24, a constant outer diameter portion 23 having the outer diameter smaller than that of the constant outer diameter portion 25, a tapered portion (distal side tapered portion) 22, and a most distal portion 21.

The first wire 2 has the tapered portions 22 and 24. Accordingly, rigidity (flexural rigidity or torsional rigidity) of the first wire 2 can be gradually reduced in the distal direction. As a result, the guide wire 1 is allowed to have satisfactory flexibility in the distal portion. Accordingly, followability to a body lumen (body-cavity) of the blood vessel and safety can be improved. Therefore, it is possible to prevent the guide wire 1 from being bent.

Each tapered angle of the tapered portions 22 and 24 (reduction rate of the outer diameter) is constant along a longitudinal direction of the wire main body 11 (hereinafter, simply referred to as a "longitudinal direction"). However, there may be a portion changing along the longitudinal direction. For example, the wire main body 11 may be formed so that a location having the relatively large tapered angle (reduction rate of the outer diameter) and a location having the relatively small tapered angle are alternately repeated multiple times.

For example, the most distal portion 21 can be a constant outer diameter portion whose outer diameter is smaller than that of the constant outer diameter portion 23.

In addition, for example, the most distal portion 21 may have a flat plate shape (ribbon shape), and may be deformable (reshaping: shaping available) into a desired shape. In general, in the guide wire 1, in order to allow the distal portion of a guiding catheter to correspond to a shape of the blood vessel or to smoothly guide the distal portion to a branch of the blood vessel, a physician uses the guide wire 1 by bending the distal portion of the guide wire 1 in advance into a desired shape in some cases. Bending the distal portion of the guide wire 1 into the desired shape in this way is called reshaping. Then, since the most distal portion 21 is provided, the reshaping can be relatively easily and reliably performed. Accordingly, operability of the guide wire 1 can be improved when the guide wire 1 is inserted into a living body.

The length of the most distal portion 21 is not particularly limited. However, the length of the most distal portion 21 can be, for example, approximately 5 mm to 200 mm, and preferably approximately 10 mm to 150 mm.

The material from which the first wire 2 is fabricated is not particularly limited. For example, the material of the first wire 2 can be various metal materials such as a Ni—Ti alloy and stainless steel can be used. However, it is preferable to use a pseudo-elastic alloy (including a super-elastic alloy). It is more preferable to use the super-elastic alloy. The super-elastic alloy is comparatively flexible, has resilience, and is less likely to be bent. Accordingly, the first wire 2 may include the super-elastic alloy. In this manner, the guide wire 1 is formed so that a distal side portion is allowed to obtain sufficient flexibility and the resilience against bending. Accordingly, followability to a complicatedly curved and bent blood vessel can be improved, and improved operability can be obtained. For example, if the first wire 2 is deformed after being repeatedly bent, the resilience of the first wire 2 allows the first wire 2 to obtain sufficient flexibility and resilience against bending. Therefore, poor operability of the guide wire 1 caused by the first wire 2 from the bending of the guide wire 1 during use can be prevented.

The distal end of the second wire 3 is joined (connected) to the proximal end (proximal end of the constant outer diameter portion 25) of the first wire 2. The second wire 3 is made from a wire rod (core material) having high rigidity. The length of the second wire 3 is not particularly limited. However, the length of the second wire 3 can be, for example, approximately 20 mm to 4,800 mm, and preferably approximately 1,400 mm to 3,000 mm.

A method of joining the first wire 2 and the second wire 3 to each other is not particularly limited. For example, various methods welding and brazing can be used. However, the first wire 2 and the second wire 3 can be joined by a welding method.

In accordance with an exemplary embodiment, the second wire 3 includes a material different from that of the first wire 2. In accordance with an exemplary embodiment, the second wire 3 may include a material having an elastic modulus (Young's modulus (longitudinal elastic modulus), a modulus of rigidity (modulus of transverse elasticity), and a bulk modulus) which is higher than the elastic modulus of the material of the first wire 2. In this manner, rigidity (flexural rigidity or torsional rigidity) suitable for the second wire 3 can be obtained, and the guide wire 1 is allowed to have a so-called strong body (i.e., such that the guide wire 1 is flexible and relatively hard to break). Accordingly, pushing performance (for example, in a distal direction) and torque transmission performance can be improved, thereby achieving improved operability.

The material from which the second wire 3 is fabricated is not particularly limited as long as the material of the second wire 3 is different from that of the first wire 2. For example, the material of the second wire 3 may be various metal materials such as stainless steel (for example, all SUS types such as SUS 304, SUS 303, SUS 316, SUS 316L, SUS316J1, SUS 316J1L, SUS 405, SUS 430, SUS 434, SUS 444, SUS 429, SUS 430F, and SUS302), a piano wire, a cobalt alloy, and a pseudo-elastic alloy. However, the material of the second wire 3 may be stainless steel or a cobalt alloy, and can be preferable that the material of the second wire 3 be stainless steel. Since the material of the second wire 3 can include stainless steel or a cobalt alloy, the guide wire 1 can obtain the improved pushing performance and torque transmission performance.

According to the present embodiment, the wire main body 11 is formed by joining the first wire 2 and the second wire 3 to each other. However, for example, without being limited thereto, the wire main body 11 may be one continuous wire rod.

As illustrated in FIG. 1, the coil 41 is installed in a distal portion and outer periphery of the wire main body 11, that is, the most distal portion 21 of the first wire 2 and the outer periphery of the distal portion of the tapered portion 22. The coil 41 having an outer diameter and an inner diameter, the outer diameter and the inner diameter being constant when installed on the outer periphery and the distal portion of the wire main body 11. The coil 41 is a member formed by winding a wire rod 40 in a spiral shape, and is installed so as to cover the distal portion of the wire main body 11, that is, the most distal portion 21 of the first wire 2, and a portion except for the proximal portion of the tapered portion 22. In addition, the first wire 2 is inserted into a substantially central portion inside the coil 41 in a non-contact manner.

The length (length of the wire main body 11 in the longitudinal direction) of the coil 41 is preferably, for example, 5 mm to 500 mm, and more preferably 10 mm to 300 mm. In addition, the inner diameter (inner diameter of the wire main body 11 in a circumferential direction) of the coil 41 is preferably, for example, 0.1 mm to 0.95 mm, and more preferably, for example, 0.2 mm to 0.7 mm.

In accordance with an exemplary embodiment, the material of the coil 41 may include a metal material. For example, the metal material of the coil 41 can include stainless steel, a super-elastic alloy, a cobalt alloy, noble metal such as gold, platinum, and tungsten, or an alloy containing these materials (for example, a platinum-iridium alloy). In particular, in a case where the material of the coil 41 includes a radiopaque material such as noble metal, the guide wire 1 is allowed to have X-ray contrast ability. While a position of the distal portion is confirmed under X-ray fluoroscopy, the guide wire 1 can be preferably inserted into a living body. In addition, in the coil 41, the distal side and the proximal side may include mutually different materials. For example, the distal side may include a coil formed of a radiopaque material, and the proximal side may be a coil formed of a material (such as stainless steel) through which X-rays are relatively transmitted.

The distal portion and the proximal portion of the coil 41 are respectively fixed to the first wire 2 by the fixing member 42 (i.e., a cap) and the fixing member 43. The fixing member 42 is disposed in the most distal portion 21. In addition, the fixing member 43 is disposed in the tapered portion 22.

These fixing members 42 and 43 can include solder (brazing filler metal) or a resin material. Without being limited to the solder, the fixing member 42 and the fixing member 43 may be an adhesive. In addition, the fixing method of the coil 41 is not limited to the method of using the fixing member. For example, the fixing method may be welding. In addition, in order to prevent damage to an inner wall of a body-cavity such as the blood vessel, a distal surface of the fixing member 42 may be rounded.

In accordance with an exemplary embodiment, the installed coil 41 on the distal portion of the guide wire 1 provides the distal portion of the guide wire 1 to obtain suitable flexibility. In addition, the first wire 2 is covered by the coil 41. In this manner, for example, a contact area with the blood vessel decreases. Accordingly, sliding resistance can be reduced. Therefore, operability of the guide wire 1 is further improved.

The coil 5 is disposed on the proximal side of the coil 41 on the outer periphery of the wire main body 11.

The coil 5 is a member formed by winding a wire rod 50, and is disposed to cover the proximal portion of the tapered portion 22 and the constant outer diameter portion 23. In addition, the wire rod 50 is a so-called "densely" wound body (i.e., tightly wound) in which adjacent portions (i.e., turns of the adjacent windings of wire rod 50) along the longitudinal direction of the guide wire 1 are in contact with each other.

In addition, the coil 5 is disposed so as not to be fixed to the wire main body 11 throughout the entire length in the longitudinal direction of the coil 5, and is also disposed so as not to be fixed to the distal member 4 (the coil 41 and the fixing member 43). In this manner, the coil 5 can be rotated independently of the wire main body 11 and the coil 41 throughout the entire length in the longitudinal direction.

In accordance with an exemplary embodiment, the length of the coil 5 as disposed on the outer periphery of the wire main body 11 in a longitudinal direction may be longer than the length of the coil 41 as disposed on the outer periphery of the wire main body 11 in a longitudinal direction. Specifically, the length of the coil 5 is preferably, for example, 10 mm to 500 mm, and more preferably, for example, 50 mm to 300 mm. In addition, the length of the coil 5 is preferably, for example, 0.3% to 30% of the length of the wire main body 11, and more preferably, for example, 1.5% to 15%. In this manner, the guide wire 1 can receive a vascular stenosed site 100 by using the coil 5 as much as possible. When the guide wire 1 is used, the coil 5 is in a state of being inserted into a body lumen such as the blood vessel.

In addition, the inner diameter and the outer diameter of the coil 5 may be equal to those of the coil 41. In particular, since the outer diameter of the coil 5 is equal to the outer diameter of the coil 41, when the guide wire 1 is viewed, it is possible to prevent or restrain a step difference from being formed in the outer periphery of the guide wire 1. Accordingly, for example, it is possible to prevent the guide wire 1 from being caught on other medical instruments such as catheters or the blood vessel.

Sliding resistance reduction processing for reducing sliding resistance between the coil 5 and the wire main body 11 may be performed on the inner peripheral portion 51 of the coil 5. According to the present embodiment, a hydrophilic lubricant layer 52 including a hydrophilic material can be coated on the inner peripheral surface of the coil 5 (refer to FIGS. 1 and 2). In this manner, the hydrophilic material is moistened and lubricated, thereby reducing friction (sliding resistance) between the coil 5 and the wire main body 11. Therefore, sliding performance can be improved.

For example, the hydrophilic material (material of the hydrophilic lubricant layer 52) can include a cellulose-based polymer material, a polyethylene oxide-based polymer material, a maleic anhydride-based polymer material (for example, a methyl vinyl ether-maleic anhydride copolymer such as a maleic anhydride copolymer), an acrylamide polymer material (for example, a block copolymer of polyacrylamide glycidyl methacrylate-dimethyl acrylamide (PGMA-DMAA)), water-soluble nylon, polyvinyl alcohol, and polyvinyl pyrrolidone.

According to the present embodiment, the hydrophilic lubricant layer 52 is disposed in the inner peripheral portion 51 of the coil 5, but may be disposed in the whole outer peripheral portion 111 of the wire main body 11. Furthermore, the hydrophilic lubricant layer 52 may be disposed in the outer peripheral portion of the coil 5. In this manner, the frictional resistance (sliding resistance) against the inner wall of the catheter used together with the guide wire 1 can be reduced. Accordingly, the sliding performance of the guide wire 1 can be improved, and the operability of the guide wire 1 inside the catheter can be satisfactorily achieved.

The example has been described in which the hydrophilic material is used as the sliding resistance reduction processing material. However, the present disclosure is not limited thereto. For example, a fluorine-based resin or a silicon-based resin may be used. The fluorine-based resin can include polytetrafluoroethylene (PTFE), ethylene-tetrafluoroethylene copolymer (ETFE), and tetrafluoroethylene-perfluoroalkylvinylether copolymer (PFA). In addition, for example, the silicon-based resin can include a silicone resin. Furthermore, a composite material of a fluorine-based resin and a silicon-based resin may be used.

In addition, the guide wire 1 can have resin coating layers 8 and 9, which resin coating layers 8 and 9 entirely or partially covering the outer peripheral surface (outer surface) of the wire main body 11. In the illustrated configuration, the resin coating layer 9 is disposed on an outer periphery of a joint portion 6 of the wire main body 11, and the resin coating layer 8 is disposed in the outer peripheral portion on the proximal side of the resin coating layer 9.

The resin coating layers 8 and 9 can be formed for various purposes. For example, the resin coating layers 8 and 9 can improve the operability of the guide wire 1 by reducing the frictional resistance (sliding resistance) of the guide wire 1 and by improving the sliding performance.

In order to reduce the frictional resistance (sliding resistance) of the guide wire 1, the resin coating layers 8 and 9 may include materials which can reduce the frictional resistance as described below. In this manner, the frictional resistance (sliding resistance) against the inner wall of the catheter used together with the guide wire 1 can be reduced. Accordingly, the sliding performance of the guide wire 1 can be improved, and the operability of the guide wire 1 inside the catheter can be satisfactorily achieved. In addition, the sliding resistance of the guide wire 1 can be reduced. Accordingly, when the guide wire 1 is moved and/or rotated inside the catheter, kink (bending) or twist of the guide wire 1, especially kink or twist in the vicinity of the joint portion (joint surface) 6 between the first wire 2 and the second wire 3 can be reliably prevented.

For example, a material of the resin coating layers 8 and 9 can include polyolefin such as polyethylene and polypropylene, polyvinyl chloride, polyester (PET or PBT), polyamide, polyimide, polyurethane, polystyrene, polycarbonate, a silicone resin, and a fluororesin (PTFE or ETFE), or a composite material of a polyolefin, such as polyethylene and polypropylene, polyvinyl chloride, polyester (PET or PBT), polyamide, polyimide, polyurethane, polystyrene, polycarbonate, a silicone resin, and a fluororesin (PTFE or ETFE).

In accordance with an exemplary embodiment, in a case of using the fluororesin (or a composite material containing the fluororesin) among the above-described materials, the frictional resistance (sliding resistance) between the guide wire 1 and the inner wall of the catheter can be effectively reduced. Accordingly, the sliding performance can be improved, and the operability of the guide wire 1 inside the catheter can be satisfactorily achieved. In addition, in this manner, when the guide wire 1 is moved and/or rotated inside the catheter, kink (bending) or twist of the guide wire 1, especially kink and twist in the vicinity of a welded portion, can be reliably prevented.

In addition, in a case of using the fluorine resin (or a composite material containing the fluorine resin), it is possible to coat the wire main body 11 with the fluorine resin in a state where the resin material is heated by burning or blowing. In this manner, adhesion between the wire main body 11 and the resin coating layers 8 and 9 is particularly excellent, for example, the adhesion between the wire main body 11 and the resin coating layers 8 and 9 are relatively high such the wire main body 11 and the resin coating layers 8 and 9 are sufficiently adhered to one another.

In addition, if the resin coating layers 8 and 9 include the silicone resin (or a composite material containing the silicone resin), when the resin coating layers 8 and 9 are formed (coated on the wire main body 11), the resin coating layer 8 reliably and firmly adhering to the wire main body 11 can be formed without heating. In accordance with an exemplary embodiment, in a case where the resin coating layers 8 and 9 include the silicone resin (or a composite material containing the silicone resin), a reactive curing type material can be used, and the resin coating layers 8 and 9 can be formed at room temperature. Since the resin coating layers 8 and 9 are formed at room temperature in this way, coating work can be relatively easily carried out, and the guide wire can be operated in a state where joining strength in the joint portion 6 is sufficiently maintained.

The materials of the resin coating layers 8 and 9 may be the same as each other or different from each other.

A thickness of the resin coating layers 8 and 9 is not particularly limited, and is appropriately selected in view of the forming purpose, the material of the resin coating layers 8 and 9, or the forming method of the resin coating layers 8 and 9. However, the thickness (average) of the resin coating layers 8 and 9 may be, for example, approximately 1 μm to 100 μm, and more preferably, for example, approximately 1 μm to 30 μm. If the thickness of the resin coating layers 8 and 9 is too thin, the forming purpose of the resin coating layers 8 and 9 may not be sufficiently achieved. In addition, if the thickness of the resin coating layers 8 and 9 is too thin, there is a possibility that the resin coating layers 8 and 9 may be separated from the wire main body 11. In addition, if the thickness of the resin coating layers 8 and 9 is too thick, there is a possibility that physical properties of the wire main body 11 may be affected. In addition, if the thickness of the resin coating layers 8 and 9 is too thick, there is a possibility that the resin coating layers 8 and 9 may be separated from the wire main body 11.

The resin coating layers 8 and 9 may be a single layer, or a stacked body of two or more layers.

In addition, according to the present disclosure, on the outer peripheral surface (surface) of the wire main body 11, processing (rough surface processing, chemical treatment, or heat treatment) for improving the adhesion of the resin coating layers 8 and 9 can be performed, or an intermediate layer capable of improving the adhesion of the resin coating layers 8 and 9 can be disposed between the resin coating layers 8 and 9 and the wire main body 11.

The guide wire 1 has the support portion 7 which supports the coil 5 from the inside (i.e., inner peripheral portion of the coil 5) so as to be rotatable around the central axis O of the wire main body 11 with respect to the wire main body 11. The support portion 7 has a distal side support portion 71 that supports the distal portion of the coil 5, and a proximal side support portion 72 that supports the proximal portion of the coil 5.

As illustrated in FIGS. 1 and 2, the distal side support portion 71 is formed to protrude to the proximal side from a fixing member main body 431 for fixing the coil 41 of the fixing member 43, and is fixed to the wire main body 11.

The distal side support portion 71 has a cylindrical shape, and is inserted into the distal portion of the coil 5. In addition, the distal side support portion 71 is disposed so as not to be fixed to the coil 5, and supports the coil 5 by being attached to the coil 5.

In addition, the outer diameter of the distal side support portion 71 is smaller than the outer diameter of the fixing member main body 431. In the manner, a stepped portion (restriction portion) 711 can be located between the fixing member main body 431 and the distal side support portion 71.

The proximal side support portion 72 is located on the proximal side from the distal side support portion 71. In addition, the proximal side support portion 72 can include a cylindrical member into which the constant outer diameter portion 23 of the wire main body 11 is inserted. The proximal side support portion 72 is fixed to the wire main body 11.

The proximal side support portion 72 has a constant outer diameter portion 721 whose outer diameter is constant and a tapered portion 722 having a tapered shape.

In accordance with an exemplary embodiment, the constant outer diameter portion 721 has an outer diameter substantially equal to an inner diameter of the coil 5, and the constant outer diameter portion 721 is inserted into the proximal portion of the coil 5. In addition, the constant outer diameter portion 721 is disposed so as not to be fixed to the coil 5, and supports the coil 5 by being attached to the coil 5.

In accordance with an exemplary embodiment, the tapered portion 722 has the largest outer diameter on the distal side, and has the smallest outer diameter on the proximal side. In addition, the tapered portion 722 has an outer diameter, which continuously and gradually decreases toward the proximal side. In this manner, it is possible to prevent a steep step difference from being located between the tapered portion 722 and the wire main body 11. Accordingly, for example, the guide wire 1 can be prevented from being caught on other medical instruments such as catheters or the blood vessel.

In addition, the largest outer diameter of the distal end of the tapered portion 722 is larger than the outer diameter of the constant outer diameter portion 721. In the manner, a stepped portion (restriction portion) 723 is located in a boundary between the constant outer diameter portion 721 and the tapered portion 722.

The distal side support portion 71 and the proximal side support portion 72 allow the coil 5 to be rotated around the central axis O with respect to the wire main body 11 throughout the entire length of the coil 5. In this manner, as illustrated in FIG. 1, even if the coil 5 is caught by the vascular stenosed site 100, if the proximal portion of the guide wire 1 is rotationally operated, the wire main body 11 and the distal member 4 can be rotated with respect to the coil 5. Accordingly, even in a state as illustrated in FIG. 1, the rotational operation can be performed, and an orientation of the distal portion of the guide wire 1 can be changed. As a result, the guide wire 1 can achieve excellent operability even inside the vascular stenosed site 100.

In the above description, as an example, a case has been described where the rotational operation is performed inside the vascular stenosed site 100. However, although not illustrated, the rotational operation can be similarly performed inside a steeply curved blood vessel. Accordingly, the guide wire 1 can achieve the excellent operability.

In accordance with an exemplary embodiment, in a natural state where an external force is not applied to the guide wire 1, the support portion 7 supports a state where the inner peripheral portion 51 of the coil 5 and the outer peripheral portion 111 of the wire main body 11 are separated from each other. In this manner, if the coil 5 and the wire main body 11 come into contact with each other, it is possible to prevent or restrain both of these from inhibiting relative rotation.

Furthermore, in the coil 5, the distal side support portion 71 and the proximal side support portion 72 can help prevent the coil 5 from being misaligned with the wire main body 11 in the radial direction, that is, the axial misalignment can be prevented. In this manner, it is possible to restrict a positional relationship in the radial direction between the coil 5 and the wire main body 11. Accordingly, when the guide wire 1 is viewed as a whole, it is possible to prevent a step difference (i.e., a difference in level between the coil 5 and the wire main body 11) from being formed due to the misalignment between the coil 5 and the wire main body 11 in the radial direction. As a result, for example, the guide wire 1 can be prevented from being caught on other medical instruments such as catheters or the blood vessel.

In addition, even if the external force is applied in a direction in which the coil 5 moves to the distal side from the position illustrated in FIGS. 1 and 2, the distal portion of the coil 5 is attached to the stepped portion 711 formed in the boundary between the distal side support portion 71 and the fixing member main body 431. In this manner, the coil 5 can be prevented from moving to the distal side further from the stepped portion 711. That is, it is possible to restrict the movement of the coil 5 to the distal side. As a result, it is possible to prevent the coil 5 from riding on the fixing member main body 431 or the coil 41.

In addition, conversely, if the external force is applied in a direction that moves the coil 5 to the proximal side from the position illustrated in FIGS. 1 and 2, the proximal portion of the coil 5 is attached to the stepped portion 723 formed between the constant outer diameter portion 721 and the tapered portion 722. In this manner, the coil 5 can be prevented from moving to the proximal side further from the stepped portion 723. That is, it is possible to restrict the movement of the coil 5 to the proximal side. As a result, it is possible to prevent the coil 5 from riding on the tapered portion 24 of the wire main body 11 or the constant outer diameter portion 25.

The material from which the distal side support portion 71 and the proximal side support portion 72 is fabricated is not particularly limited. However, it can be preferable to use a material for the distal side support portion 71 and the proximal side support portion 72, which is the same material as that of the fixing member 42 and the fixing member 43. In this manner, in a step of forming the fixing member 42 and the fixing member 43, the distal side support portion 71 and the proximal side support portion 72 can be formed. That is, in a step of fixing the coil 41 to the wire main body 11, the coil 5 can be supported by the wire main body 11. Accordingly, steps of manufacturing the guide wire 1 can be relatively simplified.

In addition, the fixing member 43 may be divided into a portion for fixing the coil 41 and a portion loosely fitted to the coil 5. In this manner, the coil 5 can smoothly rotated around the central axis O with respect to the wire main body 11.

Second Embodiment

Figure 3:
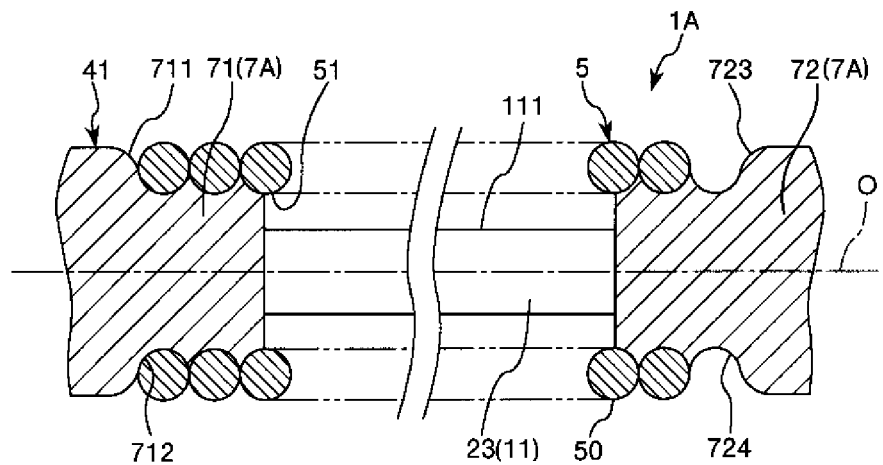
FIG. 3 is an enlarged side view (partial cross-sectional view) illustrating a tubular portion and a support portion according to a second embodiment of a guide wire.
Figure 4:
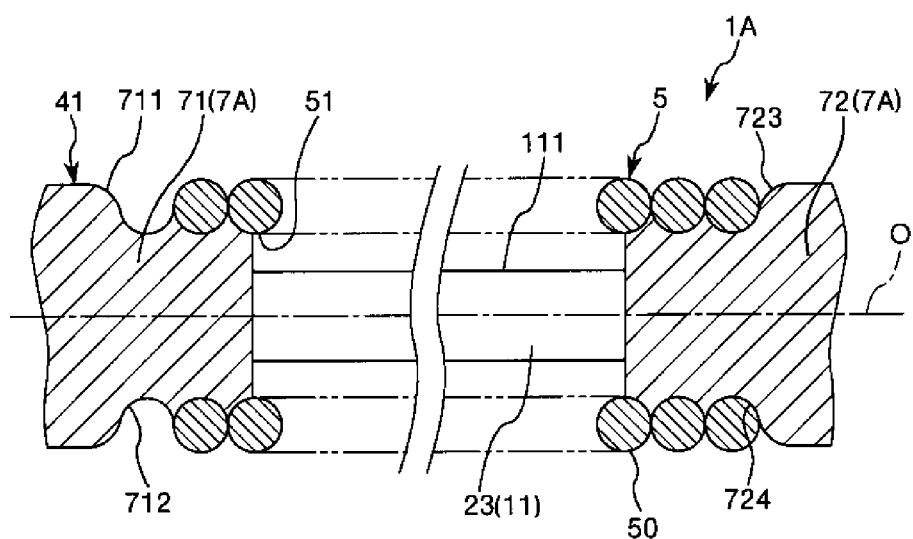
FIG. 4 is an enlarged side view (partial cross-sectional view) illustrating the tubular portion and the support portion in the second embodiment of the guide wire.

FIGS. 3 and 4 are enlarged side views (partial cross-sectional views) illustrating a tubular portion and a support portion according to a second embodiment of a guide wire of the present disclosure.

As illustrated in FIGS. 3 and 4, in a support portion 7A of a guide wire 1A, the distal side support portion 71 has a groove 712, and the proximal side support portion 72 has a groove 724.

The groove 712 is formed in a spiral shape around the central axis O in the outer peripheral portion of the distal side support portion 71. The groove 712 corresponds to a spiral shape of the wire rod 50 of the coil 5. A portion of the wire rod 50 of the coil 5 enters the groove 712. As the coil 5 is rotated, the wire rod 50 slides inside the groove 712, and the coil 5 can move in a direction of the central axis.

The groove 724 is formed in a spiral shape around the central axis O in the outer peripheral portion of the proximal side support portion 72. In addition, in the groove 724, portions of the wire rod 50 of the coil 5 adjacent to each other in the direction of the central axis O do not communicate with each other (i.e., adjacent grooves are distinguishable from each other in the direction of the central axis, and are not connected or in communication with one another). The proximal side support portion 72 of the second embodiment has a shape constituted by a convex portion and a concave portion. The convex portion can be located between the adjacent wire rods 50 of the coil 5 wound in the spiral. The proximal side support portion 72 of the first embodiment has a flat surface and does not have the convex portion or the concave portion of the second embodiment. In the second embodiment, the groove 724 corresponds to the spiral shape of the wire rod 50 of the coil 5. A portion of the wire rod 50 of the coil 5 enters the groove 724. As the coil 5 is rotated, the wire rod 50 slides inside the groove 724, and the coil 5 can move in the direction of the central axis O.

In this guide wire 1A, it is possible to bring the guide wire 1A into a state where the coil 5 is rotated with respect to the wire main body 11 and moves to the distal side with respect to the wire main body 11 (refer to FIG. 3) and a state where the coil 5 is rotated to the opposite side and moves to the proximal side with respect to the wire main body 11 (refer to FIG. 4).

In addition, as illustrated in FIG. 3, in a state where the coil 5 moves to the most distal side with respect to the wire main body 11, the stepped portion 711 restricts the coil 5 so as not to further move to the distal side. In this case, the proximal portion of the coil 5 is supported by the proximal side support portion 72.

In accordance with an exemplary embodiment, as illustrated in FIG. 4, in a state where the coil 5 moves to the most proximal side with respect to the wire main body 11, the stepped portion 723 restricts the coil 5 so as not to further move to the proximal side. In this case, the distal portion of the coil 5 is supported by the distal side support portion 71.

In this way, in the guide wire 1A, regardless of the position in the longitudinal direction in the guide wire 1A, the coil 5 is brought into a state where both ends of the coil 5 are reliably supported by the support portion 7A. Accordingly, it is possible to prevent the axial misalignment from occurring between the coil 5 and the wire main body 11.

In accordance with an exemplary embodiment, in the guide wire 1A, if a force is applied to the coil 5 in a direction in which the coil 5 moves in the direction of the central axis O, as long as the force is not applied in a direction in which the coil 5 is rotated, the coil 5 can be prevented from moving along the central axis O. In this manner, unintentional movement of the coil 5 in the direction of the central axis O can be restrained (or restricted) as much as possible.

Third Embodiment

Figure 5:
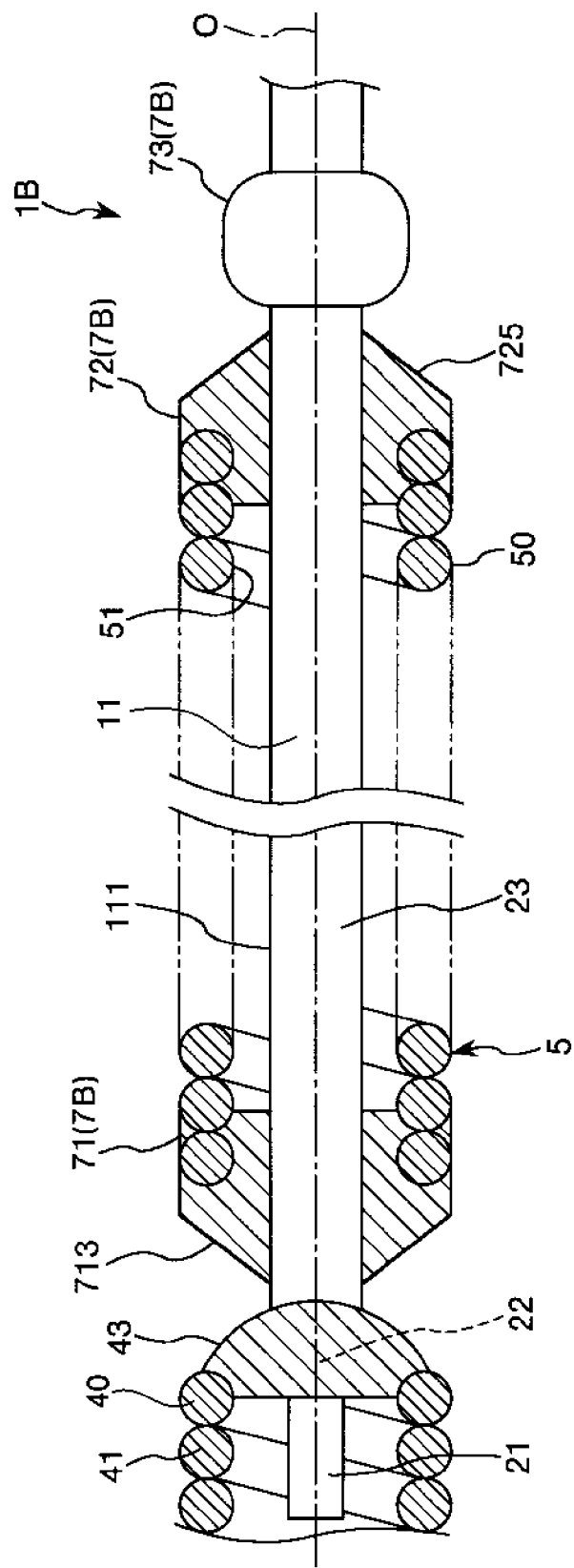
FIG. 5 is an enlarged side view (partial cross-sectional view) illustrating a tubular portion and a support portion according to a third embodiment of a guide wire.

FIG. 5 is an enlarged side view (partial cross-sectional view) illustrating a tubular portion and a support portion according to a third embodiment of a guide wire of the present disclosure.

In a support portion 7B of a guide wire 1B, the distal side support portion 71 and the proximal side support portion 72 are configured to be respectively rotatable with respect to the wire main body 11.

The distal side support portion 71 can include a cylindrical member. In addition, the distal side support portion 71 is formed to be separate from the fixing member 43. In addition, the distal portion of the distal side support portion 71 has a tapered portion 713 whose outer diameter gradually decreases in a direction away from the coil 5, that is, toward the distal side. In the addition, the distal portion of the coil 5 is buried in (i.e., distal portion of the coil 5 is embedded in the distal side support portion 71) and fixed to the distal side support portion 71.

The proximal side support portion 72 can include a cylindrical member. In addition, the proximal portion of the proximal side support portion 72 has a tapered portion 725 whose outer diameter gradually decreases toward the proximal side. In the addition, the proximal portion of the coil 5 is buried in and fixed to the proximal side support portion 72.

In addition, a support portion 7B has a ring-shaped restriction portion 73 disposed on the proximal side of the proximal side support portion 72 of the constant outer diameter portion 23 of the wire main body 11. The restriction portion 73 is fixed to the constant outer diameter portion 23 of the wire body 11. In this manner, the support portion 7B can be restricted so as not to move to the proximal side from the restriction portion 73.

In this guide wire 1B, when a force is applied in a direction in which the coil 5 is rotated around the central axis O, while the coil 5 is supported by the distal side support portion 71 and the proximal side support portion 72, the coil 5 is rotated together with the distal side support portion 71 and the proximal side support portion 72 with respect to the wire main body 11. In this manner, the coil 5 can be stably rotated. As a result, it is possible to reliably prevent the axial misalignment from occurring between the coil 5 and the wire main body 11.

Furthermore, the tapered portion 713 and the tapered portion 725 can reliably prevent the coil 5 from riding on the coil 41 or riding on the restriction portion 73.

Although not illustrated, according to the present embodiment, the sliding resistance reduction processing as described in the first embodiment may be performed on the inner peripheral surface of the distal side support portion 71 and the proximal side support portion 72. In this manner, the coil 5 can be smoothly rotated around the central axis O with respect to the wire main body 11.

Fourth Embodiment

Figure 6:
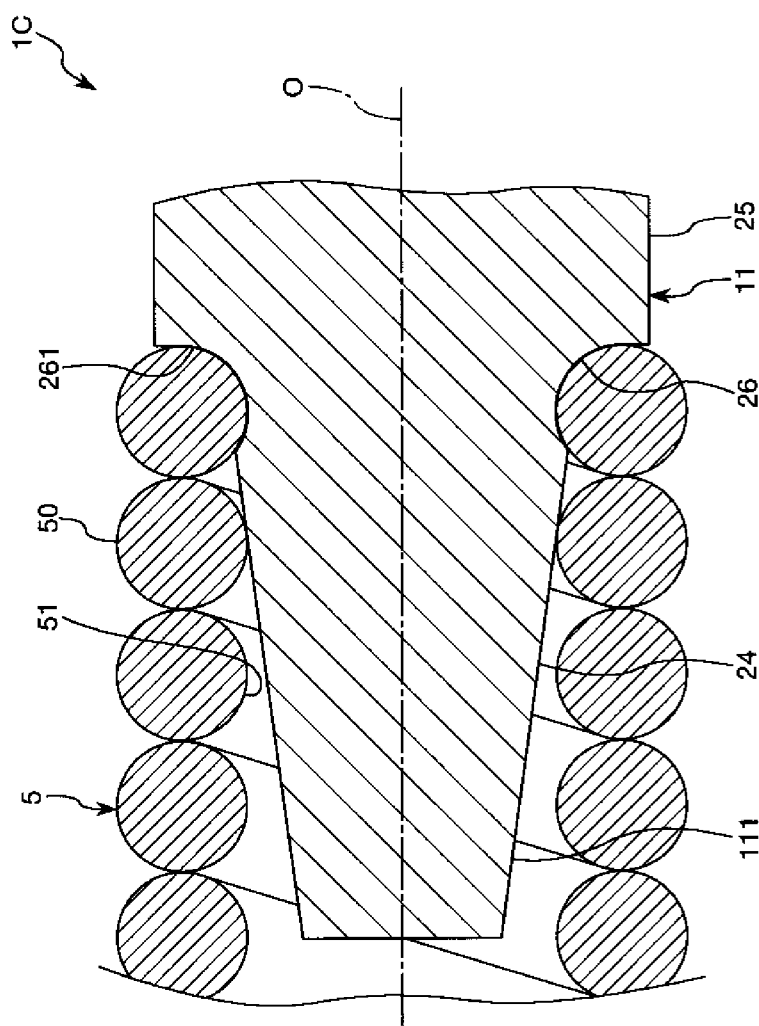
FIG. 6 is an enlarged cross-sectional view illustrating a tubular portion and a support portion according to a fourth embodiment of a guide wire.

FIG. 6 is an enlarged cross-sectional view illustrating a tubular portion and a support portion according to a fourth embodiment of a guide wire of the present disclosure.

In a guide wire 1C, a groove 26 is disposed in a boundary portion between the tapered portion 24 of the wire main body 11 and the constant outer diameter portion 25. The groove 26 can include a ring-shaped groove located along the circumferential direction of the wire main body 11. The wire rod 50 of the proximal portion of the coil 5 is inserted into the groove 26. In this state, an inserted portion of the wire rod 50 of the coil 5 is supported by the inner peripheral portion 261 of the groove 26 so as to be rotatable around the central axis O. Furthermore, in this state, the inserted portion of the wire rod 50 is restricted by the inner peripheral portion 261 of the groove 26 so as not to move to the proximal side.

In this way, according to the guide wire 1C, the groove 26 of the wire main body 11 functions as the proximal side support portion. In this manner, an advantageous effect the same as that according to the first embodiment can be achieved, and the formation of the proximal side support portion 72 according to the first embodiment can be omitted. Therefore, manufacturing steps of the guide wire 1C can be simplified. Furthermore, according to the present embodiment, the coil 5 is restricted so as not to move to the proximal side. Therefore, it is possible to improve the operability.

Fifth Embodiment

Figure 7:
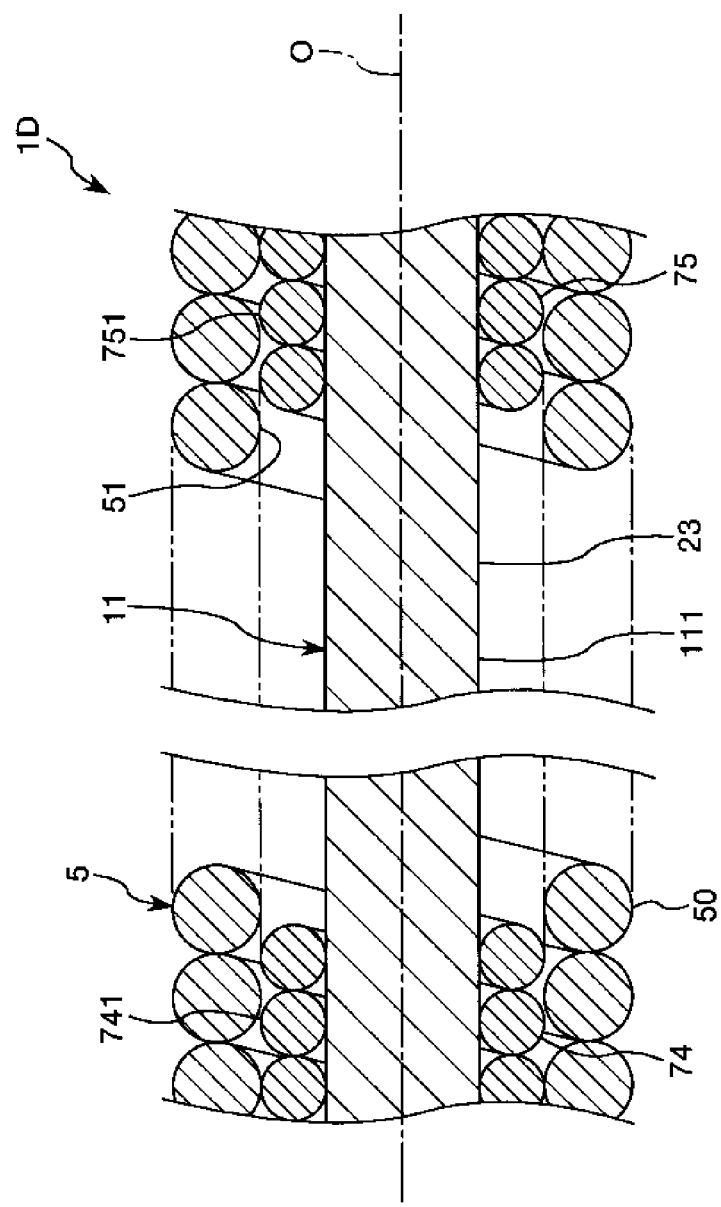
FIG. 7 is an enlarged cross-sectional view illustrating a tubular portion and a support portion according to a fifth embodiment of a guide wire.

FIG. 7 is an enlarged cross-sectional view illustrating a tubular portion and a support portion according to a fifth embodiment of a guide wire of the present disclosure.

In a guide wire 1D, coils 74 and 75 are disposed between the constant outer diameter portion 23 of the wire main body 11 and the coil 5.

The coil 74 is disposed between the distal portion of the coil 5 and the constant outer diameter portion 23. The coil 74 is a member in which a wire rod 741 is wound around the central axis O. The coil 74 is shorter in length than the coil 5, and an outer peripheral portion of the coil 74 is fixed to the coil 5. In addition, the coil 74 has an inner peripheral portion attached to the constant outer diameter portion 23, and is rotatable with respect to the wire main body 11.

The coil 75 is disposed between the proximal portion of the coil 5 and the constant outer diameter portion 23. The coil 75 is a member in which a wire rod 751 is wound around the central axis O. The coil 75 is shorter in length than the coil 5, and an outer peripheral portion of the coil 75 is fixed to the coil 5 via an adhesive layer (not illustrated). In addition, the coil 75 has an inner peripheral portion attached to the constant outer diameter portion 23, and is rotatable with respect to the wire main body 11.

In this guide wire 1D, while the coil 5 is supported by the coils 74 and 75, the coil 5 together with the coil 74 and the coil 75 can be rotated with respect to the wire main body 11. Accordingly, it is possible to achieve an advantageous effect the same as that of the above-described respective embodiments.

The coil 74 and the coil 75 may be formed integrally with the coil 5. In the coil 5, the distal portion and the proximal portion may be configured so that the wire rod 50 is wound double (or twice) and the doubled portions overlap each other in the radial direction. In this manner, manufacturing steps of the guide wire 1D can be further simplified.

The guide wire according to the present disclosure has been described with reference to the embodiments illustrated in the drawings. However, the present disclosure is not limited thereto, and the configuration of each unit may be substituted with any desired configuration having the same function. In addition, any other desired configuration may be added to the present disclosure.

In the respective embodiments, a case has been described where the tubular portion includes a coil. However, the present disclosure is not limited thereto. For example, the tubular portion may include a tubular member or a member in which a plurality or multiple rings are concentrically located and connected to each other.

In addition, according to the above-described respective embodiments, a cross-sectional shape of the wire rod of each of the coils has a circular shape. However, the present disclosure is not limited thereto. For example, a semicircular shape or a flat shape may be used.

In addition, the above-described respective embodiments adopt a configuration in which the support portion supports both end portions of the tubular portion. The present disclosure is not limited thereto. As long as the support portion has a function to support at least one end portion of the distal portion and the proximal portion, the advantageous effect according to the present disclosure is achieved.

A guide wire according to the present disclosure includes a flexible wire main body, a tubular portion that is intermediately disposed in a longitudinal direction of the wire main body in an outer periphery of the wire main body, and that has a tubular shape, and a support portion that supports at least one end portion of a distal portion and a proximal portion of the tubular portion from the inside so as to be rotatable around a central axis of the wire main body. Therefore, the tubular portion is rotatable with respect to the wire main body. Accordingly, for example, even if the tubular portion is caught by a stenosed site, the wire main body can be rotationally operated.

The detailed description above describes a guide wire. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
a flexible wire main body;
a tubular portion that is intermediately disposed in a longitudinal direction of the wire main body in an outer periphery of the wire main body, the tubular portion having a tubular shape;
a support portion including a distal side support portion that supports a distal portion of the tubular portion and a proximal side support portion that supports a proximal portion of the tubular portion on an inner periphery of the tubular portion and wherein the support portion is configured to be rotatable around a central axis of the wire main body; and
the proximal side support portion including a cylindrical member into which a constant outer diameter portion of the flexible wire main body is inserted, and the proximal side support portion including a constant outer diameter portion and a tapered portion, the tapered portion having a larger outer diameter on a distal side and a smaller outer diameter on a proximal side.

2. The guide wire according to claim 1, wherein in a natural state where an external force is not applied to the guide wire, the support portion supports in a state where an inner peripheral portion of the tubular portion and an outer peripheral portion of the wire main body are separated from each other.

3. The guide wire according to claim 1, wherein the support portion is fixed to the wire main body.

4. The guide wire according to claim 3, wherein the tubular portion comprises a coil formed of a wire rod wound in a spiral shape.

5. The guide wire according to claim 4, further comprising:
a spiral groove into which the wire rod is inserted is disposed in an outer peripheral portion of the distal side support portion and an outer peripheral portion of the proximal side support portion.

6. The guide wire according to claim 3, further comprising:
a distal coil that is disposed on a distal side from the tubular portion in a distal outer peripheral portion of the wire main body; and
a fixing portion that fixes a proximal portion of the distal coil to the wire main body.

7. The guide wire according to claim 6, wherein the support portion is formed integrally with the fixing portion.

8. The guide wire according to claim 1, wherein the support portion is configured to be rotatable around the central axis of the wire main body with respect to the wire main body.

9. The guide wire according to claim 8, wherein the support portion and the tubular portion are fixed to each other.

10. The guide wire according to claim 8, further comprising:
a distal coil that is disposed on a distal side from the tubular portion in a distal outer peripheral portion of the wire main body; and
an inner diameter of the support portion being smaller than an outer diameter of the distal coil.

11. The guide wire according to claim 1, further comprising:
a restriction portion that restricts movement of the tubular portion in the longitudinal direction of the wire main body formed between a boundary of the constant outer diameter portion and the tapered portion.

12. The guide wire according to claim 1, wherein the larger outer diameter of the tapered portion is larger than an outer diameter of the constant outer diameter portion.

13. A guide wire comprising:
a flexible wire main body;
a tubular portion that is intermediately disposed in a longitudinal direction of the wire main body in an outer periphery of the wire main body, the tubular portion having a tubular shape;
a support portion including a distal side support portion that supports at least a distal portion of the tubular portion and a proximal side support portion that supports a proximal portion of the tubular portion on an inner periphery of the tubular portion and wherein the support portion is configured to be rotatable around a central axis of the wire main body;
the proximal side support portion including a cylindrical member into which a constant outer diameter portion of the flexible wire main body is inserted, and the proximal side support portion including a constant outer diameter portion and a tapered portion, the tapered portion having a larger outer diameter on a distal side and a smaller outer diameter on a proximal side; and at least a portion of the support portion is located between the outer periphery of the wire main body and the inner periphery of the tubular portion in at least one of the distal portion and the proximal portion of the tubular portion.

14. The guide wire according to claim 13, wherein in a natural state where an external force is not applied to the guide wire, the support portion supports in a state where an inner peripheral portion of the tubular portion and an outer peripheral portion of the wire main body are separated from each other.

15. The guide wire according to claim 13, wherein the support portion is fixed to the wire main body.

16. The guide wire according to claim 15, wherein the tubular portion comprises a coil formed of a wire rod wound in a spiral shape;

the support portion having a cylindrical shape; and a spiral groove into which the wire rod is inserted is disposed in an outer peripheral portion of the support portion.

17. A guide wire comprising:

a flexible wire main body;

a tubular portion that is intermediately disposed in a longitudinal direction of the wire main body in an outer periphery of the wire main body, and wherein the tubular portion has a tubular shape having a lumen;

a support portion including a distal side support portion that supports at least a distal portion of the tubular portion and a proximal side support portion that supports a proximal portion of the tubular portion on an inner periphery of the tubular portion and wherein the support portion is configured to be rotatable around a central axis of the wire main body;

the proximal side support portion including a cylindrical member into which a constant outer diameter portion of the flexible wire main body is inserted, and the proximal side support portion including a constant outer diameter portion and a tapered portion, the tapered portion having a larger outer diameter on a distal side and a smaller outer diameter on a proximal side;

the support portion including a protruding portion which protrudes along the central axis; and wherein the protruding portion is inserted into the lumen of the tubular portion from at least one of the distal portion and the proximal portion of the tubular portion.

18. The guide wire according to claim 17, wherein the support portion is fixed to the wire main body.

19. The guide wire according to claim 18, wherein the tubular portion comprises a coil formed of a wire rod wound in a spiral shape; and the support portion having a cylindrical shape.

20. The guide wire according to claim 18, further comprising: a distal coil that is disposed on a distal side from the tubular portion in a distal outer peripheral portion of the wire main body; and a fixing portion that fixes a proximal portion of the distal coil to the wire main body.

\* \* \* \* \*